United States Patent [19]

Ninomiya et al.

[11] Patent Number: 4,695,568
[45] Date of Patent: Sep. 22, 1987

[54] THIENO[2,3-D]PYRIMIDINE DERIVATIVES AND SALTS THEREOF

[75] Inventors: Kunihiro Ninomiya; Issei Nitta, both of Machida; Akihiro Tobe, Yokohama; Mitsuo Egawa; Ryoji Kikumoto, both of Machida, all of Japan

[73] Assignee: Mitsubishi Chemical Industries Limited, Tokyo, Japan

[21] Appl. No.: 685,768

[22] Filed: Dec. 24, 1984

[30] Foreign Application Priority Data

Jan. 5, 1984 [JP] Japan ................................. 59-479

[51] Int. Cl.[4] ..................... A61K 31/38; C07D 239/00
[52] U.S. Cl. .................................. 514/258; 514/267; 544/250; 544/278
[58] Field of Search ................. 544/278, 250; 514/258

[56] References Cited

U.S. PATENT DOCUMENTS

| | | | |
|---|---|---|---|
| 3,883,651 | 5/1975 | Woitun et al. | 514/258 |
| 4,054,656 | 10/1977 | Temple, Jr. | 514/258 |
| 4,146,716 | 3/1979 | Cox et al. | 544/250 |
| 4,196,207 | 4/1980 | Webber | 514/258 |
| 4,471,117 | 9/1984 | Sipido | 544/250 |

FOREIGN PATENT DOCUMENTS 87337  8/1983  European Pat. Off.
56-92875  7/1981  Japan.

OTHER PUBLICATIONS

Ishikawa, F., et al, *Chem. Pharm. Bull.*, 28, 3172-3177 (1980).

*Primary Examiner*—Nicholas S. Rizzo
*Assistant Examiner*—Barbara Cassatt
*Attorney, Agent, or Firm*—Oblon, Fisher, Spivak, McClelland & Maier

[57] ABSTRACT

This invention relates novel thieno[2,3-d]pyrimidine derivatives represented by the following general formula (I):

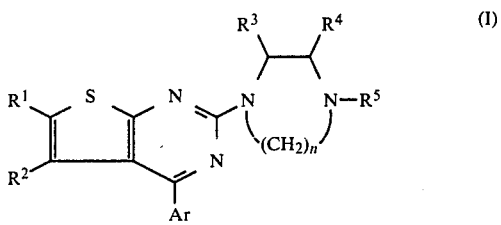

or salts thereof; wherein $R^1$ and $R^2$ independently represent hydrogen, halogen or alkyl group having 1 to 6 carbon atoms; or $R^1$ and $R^2$ may concatenate to form a cycloalkylene group having 5 or 6 ring carbon atoms; $R^3$ and $R^4$ independently represent hydrogen or alkyl group having 1 to 6 carbon atoms; $R^5$ represents a member selected from (1) hydrogen or alkyl having 1 to 6 carbon atoms,
(2)

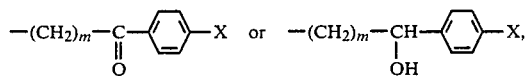

in which m is an integer of from 1 to 3 and X represents halogen, or
(3)

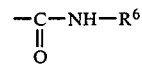

in which $R^6$ represents alkyl group having 1 to 6 carbon atoms;

Ar represents substituted or unsubstituted phenyl, or 2- or 3-thienyl group; and n is 2 or 3. The derivatives of the invention can be used in the treatment of the various depression disease or the higher dysfunction of the brain.

18 Claims, No Drawings

THIENO[2,3-D]PYRIMIDINE DERIVATIVES AND SALTS THEREOF

This invention relates to novel thieno[2,3-d]pyrimidine derivatives and salts thereof.

We have done many investigations onto compounds having a psychotropic activity and finally found thieno[2,3-d]pyrimidine derivatives having piperazinyl or homopiperazinyl group on 2-position and phenyl or thienyl group on 4-position which show such a psychotropic activity. These findings have led us to the present invention.

It is an object of the invention, therefore, to provide a thieno[2,3-d]pyrimidine derivative represented by the following general formula (I):

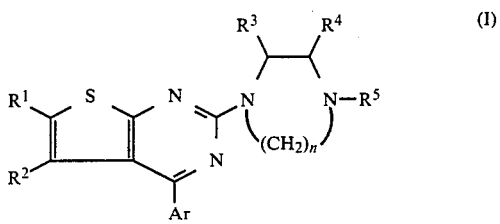

wherein $R^1$ and $R^2$ independently represent hydrogen, halogen (preferably fluorine, chlorine, bromine, iodine and the like), or alkyl group containing 1-6 carbon atoms, preferably 1-4 carbon atoms, such as methyl, ethyl, propyl, butyl and the like; or alternatively $R^1$ and $R^2$ may form a 5- or 6-membered cycloalkylene ring together with two carbon atoms of thienyl group; $R^3$ and $R^4$ independently represent hydrogen or alkyl group containing 1-6 carbon atoms, preferably 1-4 carbon atoms, such as methyl, ethyl, propyl, butyl and the like; $R^5$ represents (1) hydrogen or alkyl group containing 1-6 carbon atoms, preferably 1-4 carbon atoms, such as methyl, ethyl, propyl, butyl and the like, (2)

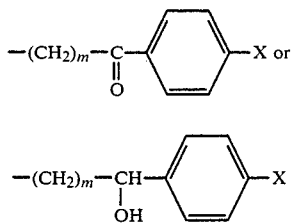

in which m is an integer of 1-3 and X represents halogen such as fluorine, chlorine, bromine, iodine and the like, or (3)

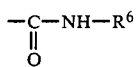

in which $R^6$ represents alkyl group containing 1-6 carbon atoms, preferably 1-4 carbon atoms, such as methyl, ethyl, propyl, butyl and the like; Ar represents phenyl or 2- or 3-thienyl group which may substituted; and n is 2 or 3, and a salt thereof.

When phenyl group represented by Ar is substituted, the substituent may be halogen such as fluorine, chlorine, bromine, iodine and the like; alkyl group containing 1-6 carbon atoms such as methyl, ethyl, propyl, butyl, hexyl and the like; alkoxy group containing 1-6 carbon atoms such as methoxy, ethoxy, propoxy, butoxy and the like; hydroxyl group; nitro group; amino group; cyano group; or alkyl-substituted amino group such as methylamino, ethylamino, dimethylamino, diethylamino group.

The thieno[2,3-d]pyrimidine derivatives of the invention may be prepared in accordance with any one of the following processes.

Process (a):

A compound having the general formula (II):

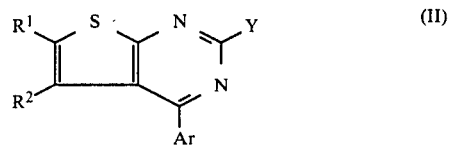

wherein $R^1$, $R^2$ and Ar are as defined above and Y represents halogen, is reacted with an amine represented by the general formula (III) or (IV):

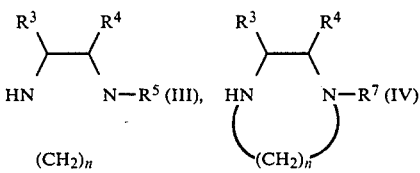

wherein $R^3$-$R^5$ and n are as defined hereinafore and $R^7$ represents a protective group of an amino group. When an amine of the general formula (IV) is used, a deprotection of the group $R^7$ should be required to obtain a compound of the formula (I). The protective groups represented by $R^7$ are benzyl, formyl, acetyl, benzyloxycarbonyl group and the like.

In the reaction of the pyrimidine derivative of (II) with an amine of (III) or (IV), at least two equivalents of amine are preferably used since one equivalent of the amine used is utilized for eliminating the hydrogenhalide formed. In order to promote the reaction, the amine (III) or (IV) may often preferably be used in an excess amount up to 20 equivalents.

When the reaction is carried out with 1 equivalent of amine, an acid binding agent such as a tertiary amine, potassium carbonate and sodium carbonate is added to the reaction mixture. When the reaction is carried out with an excess amount of amine, the reaction may proceed with or without a solvent. The solvent which may be used in the reaction is for example inert organic solvents such as alcohols with 1-8 carbon atoms, tetrahydrofuran, dioxane, benzene, benzene substituted with alkyl group(s) or halogen(s), chloroform, di- or trichloroethylene, acetonitrile, dimethylformamide, dimethylsulfoxide, and the like, and any mixture thereof. The reaction is generally carried out at a temperature in the range of 20°-200° C., preferably in the range of 50°-100° C.

The starting compound, that is, the pyrimidine derivatives represented by the general formula (II) may be prepared according to the method described in Chem. Pharm. Bull., 28(11), 3172(1980).

When an amine represented by the general formula (IV) is used in this process, the protective group $R^7$ for the amino group should be eliminated for obtaining the product (I) in which $R^5$ is hydrogen after the completion of the reaction. For example, the protective group R[7] of benzyl or benzyloxycarbonyl group can be eliminated by catalytic hydrogen using palladium carbon as a catalyst. R[7] of formyl or acetyl group can be eliminated by acid hydrolysis.

Process (b):

When a compound of the general formula (I) in which R[5] is not hydrogen may be prepared, a pyrimidine derivative represented by the general formula (V) may be reacted with a compound represented by the general formula (VI) or an alkylisocyanate represented by the general formula (VII) in accordance with the following reaction formula:

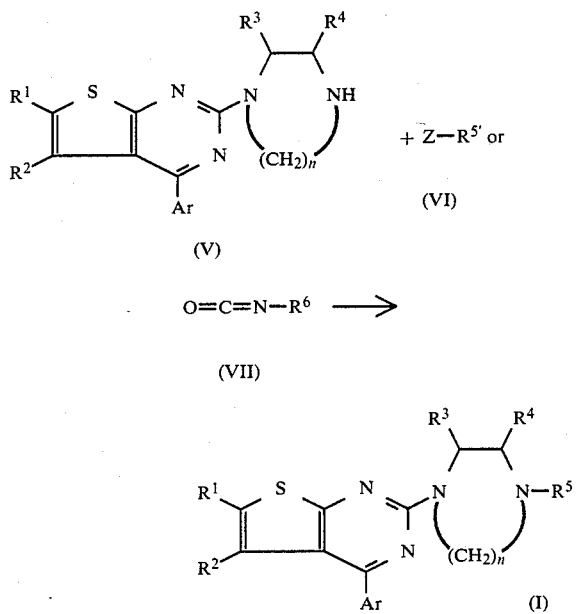

wherein R[1]-R[5], n and Ar are as defined previously, provided that R[5] is not hydrogen, Z represents a halogen atom, R[5'] is as defined previously in (1) and (2) of R[5], provided that R[5'] is other than hydrogen atom, and R[6] is as defined previously in (3) of R[5].

The pyrimidine derivative (V) may be a product of the process (a) described above.

The reaction between the pyrimidine derivative (V) and a compound of (VI) can be carried out in a solvent such as acetone, methylethylketone, dimethylformamide, dimethylsulfoxide and the like with the use of potassium carbonate or sodium carbonate as an acid binding agent.

The reaction of the pyrimidine derivative (V) with an alkylisocyanate (VII) may be carried out at room temperature in a solvent such as dichloromethane, chloroform and the like.

Process (c):

A compound of the general formula (I) obtained by the process (a) or (b) can be subjected to a further reaction to convert the substituent Ar or R[5] to another substituent. Thus, another compound included within the scope of the general formula (I) may be obtained.

For example, a substituent on the group Ar can be converted to another substituent. An example of such a conversion is conversion of nitro group to amino group by iron powderacetic acid, conversion of bromo group to cyano group by cuprous cyanide in dimethylformamide, or the like. An example of the conversion of the group R[5] is conversion of p-fluorophenacyl group to 2-(4-fluorophenyl)-2-hydroxyethyl group by sodium borohydride, or the like.

Preferred compounds represented by the general formula (I) which may be prepared by the method (a), (b) or (c) include: 6-methyl-4-phenyl-2-piperazinyl-thieno[2,3-d]pyrimidine; 5,6-dimethyl-4-phenyl-2-piperazinyl-thieno[2,3-d]pyrimidine; 5-methyl-4-phenyl-2-piperazinyl-thieno[2,3-d]pyrimidine; 6-chloro-4-phenyl-2-piperazinyl-thieno[2,3-d]pyrimidine; 4-(2-fluorophenyl)-6-methyl-2-piperazinyl-thieno[2,3-d]pyrimidine; 4-(2-bromophenyl)-6-methyl-2-piperazinyl-thieno[2,3-d]pyrimidine; 6-methyl-4-(2-methylphenyl)-2-piperazinyl-thieno[2,3-d]pyrimidine; 4-(2-cyanophenyl)-6-methyl-2-piperazinyl-thieno[2,3-d]pyrimidine; and the like.

A pharmaceutically acceptable acid addition salt of thieno[2,3-d]pyrimidine derivative represented by the general formula (I) is also included in the scope of the present invention. Such an acid addition salt includes those of an inorganic acid such as hydrochloric acid, phosphoric acid, sulfuric acid and the like, and those of an organic acid such as acetic acid, formic acid, citric acid, p-toluenesulfonic acid and the like.

The thieno[2,3-d]pyrimidine derivatives of the invention have pharmaceutically useful activities, particularly for the central nervous system. Indeed, the compound of the invention has an antagonistic activity against the hypothermal activity of reserpine and an activity for improving the reduction of passive avoidance reaction on an electric shock, which is a model of dysmnesia. Due to such activities, the compounds of the invention are preferably utilized as a pharmaceutical preparation for improvement of intellectual disturbance or depression.

The compound of the invention may be administered solely or in admixture with pharmaceutically acceptable carrier. The composition of a preparation for such use can be varied according to the solubility or chemical properties of the compound or dosage routes or administration plan.

For example, for parenteral administration, such as intramuscular, intravenous or hypodermic injection, the compound of the invention may be made into a sterilized isotonic solution supplemented with other solutes such as sodium chloride, glucose and the like. The compound can also be administered orally in the form of a tablet, capsule or granule which contains a suitable vehicle, for example, starch, lactose, sucrose or the like. A cachou, such as troch and lozenge, which may be prepared by mixing the compound of the invention with sugar, corn syrup, essence, coloring matter etc., dehydrating and solidifying, can also be used. Further, the compound can also be administered orally as a solution containing a coloring matter and essence.

A dose of the preparation containing the compound of the invention may be decided by a physician according to the dosage method, the kind of the compound and/or the conditions of a patient to be treated.

Generally, a daily dose of the compound is 0.1–50 mg/kg for parenteral administration, or 0.5–500 mg/kg for oral administration.

The invention will be further illustrated hereinafter by the non-limitative examples. These examples do not limit the invention and many variations and modifications may be made without departing the scope of the present invention.

EXAMPLE 1

PREPARATION OF 6-METHYL-4-PHENYL-2-PIPERAZINYL-THIENO[2,3-d]PYRIMIDINE BY PROCESS (A)

Into a solution of 62 g of anhydrous piperazine dissolved with heating in 100 ml of ethanol, 15.64 g of 2-chloro-6-methyl-4-phenyl-thieno[2,3-d]pyrimidine dissolved in 40 ml of warm chlorofrom is added dropwise under reflux. The mixture is further heated under reflux for an additional hour. Chloroform and ethanol are distilled off under reduced pressure. To the product are added 300 ml of chloroform and 300 ml of water, and then the product is extracted into the chloroform layer. The chloroform layer is washed twice with 200 ml of water and then with saturated aqueous sodium chloride solution, and dried over anhydrous sodium sulfate. The chloroform layer containing the product is concentrated and crystallized from chloroform/cyclohexane. There is obtained 17.17 g of the product in the form of free base, melting point of 186°–187° C. The product is dissolved in 60 ml of chloroform by heating. To the resultant solution, 1.1 equivalents of 20% solution of hydrogen chloride in ethanol and then 350 ml of ethanol are succeedingly added. After 100 ml of the solvent is distilled off under reduced pressure and allowed to cool, the deposited crystal is filtered out to obtain 18.20 g of mono hydrochloride salt of the product which has a melting point of 270°–280° C. (decompose).

EXAMPLES 2–21

The procedures of Example 1 are repeated and the compounds shown in Table 1 are obtained from the corresponding 2-chloro-thieno[2,3-d]pyrimidines and piperazines or homopiperazines.

TABLE 1

| Example No. | $R^1$ | $R^2$ | n | $R^4$ | Ar | Free Base (°C.) | Monohydrochloride (°C.) |
|---|---|---|---|---|---|---|---|
| 1 | CH₃ | H | 2 | H |  | 186–187 | 270–280 (decomp.) |
| 2 | H | H | 2 | H |  | 122–123.5 | 270–285 (decomp.) |
| 3 | C₂H₅ | H | 2 | H |  | 107–110 | 263–268 (decomp.) |
| 4 | CH₃ | CH₃ | 2 | H |  | 188.5–189.5 | 261–180 (decomp.) |
| 5 | H | CH₃ | 2 | H |  | — | 266–272 (decomp.) |
| 6 | H | C₂H₅ | 2 | H |  | — | 263–273 (decomp.) |
| 7 | Cl | H | 2 | H |  | 174–175 | 282–295 (decomp.) |
| 8 | Br | H | 2 | H |  | 173–175 | — |
| 9 | CH₃ | H | 3 | H |  | 142–144 | 268–282 (decomp.) |
| 10 | CH₃ | H | 2 | CH₃ |  | 138–140 | 270–285 (decomp.) |
| 11 | CH₃ | H | 2 | H |  | — | 272–280 (decomp.) |
| 12 | CH₃ | H | 2 | H |  | 134–136 | 267–274 (decomp.) |
| 13 | CH₃ | H | 2 | H |  | 215–217 | 295–310 (decomp.) |
| 14 | CH₃ | H | 2 | H |  | 155–156 | 270–283 (decomp.) |
| 15 | CH₃ | H | 2 | H |  | — | 285–295 (decomp.) |
| 16 | CH₃ | H | 2 | H |  | 89–91 | 270–283 (decomp.) |
| 17 | CH₃ | H | 2 | H |  | 172–174 | 265–271 (decomp.) |
| 18 | CH₃ | H | 2 | H |  | 194–197 | 288–300 (decomp.) |
| 19 | CH₃ | H | 2 | H |  | — | 300–310 (decomp.) |
| 20 | CH₃ | H | 2 | H |  | 150–152 | 289–298 (decomp.) |
| 21 | CH₃ | H | 2 | H |  | 168–169 | 283–295 (decomp.) |

EXAMPLE 22

PREPARATION OF 6-METHYL-2-(2-METHYLPIPERAZINYL)-4-PHENYL-THIENO[2,3-d]PYRIMIDINE BY PROCESS (A): DEPROTECTION OF AMINO GROUP

A mixture of 3 g of 2-chloro-6-methyl-4-phenyl-thieno[2,3-d]pyrimidine, 2.2 g of 1-benzyl-3-methylpiperazine, 1.1 g of sodum carbonate and 4 ml of dimethylformamide is reacted under reflux for 3 hours. After cooling, 80 ml of benzene and 80 ml of water are added and two layers are separated. The benzene layer is washed twice with 100 ml of water and then with saturated aqueous sodium chloride solution, and dried over anhydrous sodium sulfate. After distilling off benzene, purification of the product by silica gel chromatography using 180 g of silica gel and n-hexane/ethyl acetate (10:1) as an eluent is carried out. There is obtained 4.3 g of oily 2-(4-benzyl-2-methylpiperazinyl)-6-methyl-4-phenyl-thieno[2,3-d]pyrimidine.

The protected material is dissolved in a mixed solvent of 90 ml of acetic acid and 10 ml of concentrated hydrochloric acid. The resulting solution is subjected to catalytic hydrogenation at 70° C. under atmospheric pressure for 4 hours using 0.5 g of palladium black as a catalyst. After filtering out the catalyst, acetic acid and hydrochloric acid are distilled off. 150 ml of ethyl acetate and 100 ml of 10% aqueous solution of potassium carbonate and two layers are separated. The ethyl acetate layer is washed with water and then with saturated aqueous solution of sodium chloride, and dried over anhydrous sodium sulfate. After distilling off ethyl acetate, recrystallization from chloroform/n-hexane gives 1.85 g of the desired product with a melting point of 168°–170° C.

EXAMPLE 23

PREPARATION OF 2-(4-(4-FLUOROPHENACYL)-PIPERAZINYL)-6-METHYL-4-PHENYL-THIENO[2,3-d]PYRIMIDINE BY PROCESS (B)

In 6 ml of methylethylketone, 2.03 g of 6-methyl-4-phenyl-2-piperazinyl-thieno[2,3-d]pyrimidine, 1.25 g of 4-fluorophenacyl chloride and 0.73 g of triethylamine are reacted under reflux for 5 hours. After cooling, 70 ml of chloroform is added to the reaction mixture. The solution is washed twice with 100 ml of water and then saturated aqueous solution of sodium chloride, and dried over anhydrous sodium sulfate. After distilling off chloroform, crystallization from diethylether/methanol gives 2.68 g of the product which has a melting point of 141°–142° C.

EXAMPLE 24

PREPARATION OF 2-(4-(2-(4-FLUOROPHENYL)-2-HYDROXYETHYL)-PIPERAZINYL)-6-METHYL-4-PHENYL-THIENO[2,3-d]PYRIMIDINE BY PROCESS (C): CONVERSION OF $R^5$

Into a mixture of 10 ml of chloroform and 10 ml of ethanol is dissolved 1.34 g of 2-(4-(4-fluorophenacyl)-piperazinyl)-6-methyl-4-phenyl-thieno[2,3-d]pyrimidine, and then 0.23 g of sodium borohydride is added at room temperature. After reaction for one hour, 60 ml of chloroform and 100 ml of water are added and two layers are separated. The chloroform layer is washed with 100 ml of water and then with saturated aqueous solution of sodium chloride, and dried over anhydrous sodium sulfate. Chloroform is distilled off and 1.27 g of the desired crystal is obtained from methanol. The product has a melting point of 180°–181.5° C.

EXAMPLE 25

PREPARATION OF 4-(2-AMINOPHENYL)-6-METHYL-2-PIPERAZINYL-THIENO[2,3-d]PYRIMIDINE BY PROCESS (C): CONVERSION OF SUBSTITUENT ON THE GROUP Ar

Into a mixed solvent of 8 ml of ethanol, 3.5 ml of water and 4 ml of acetic acid, 1.25 g of 6-methyl-4-(2-nitrophenyl)-2-piperazinyl-thieno[2,3-d]pyrimidine is dissolved, and 1.5 g of iron powder is gradually added at 90° C. over one hour. After the reaction at 90° C. further for 20 minutes, 25 ml of ethanol and 6 ml of water are added. The reaction mixture is filtered by a Celite layer. The Celite layer is washed with hot ethanol and the washings and the filtrate are combined and distilled off under reduced pressure. The residue is treated with 20 ml of 10% aqueous solution of sodium carbonate and with 80 ml of chloroform and filtered by a Celite layer. The chloroform layer is separated and dried over anhydrous sodium sulfate. Chloroform is removed to concentrate and crystallization from chloroform/cyclohexane gives the desired product (0.93 g) which has a melting point of 232°–236° C.

EXAMPLE 26

PHARMACOLOGICAL TESTS

A. ANTAGONISTIC ACTIVITY AGAINST RESERPINE-INDUCED HYPOTHERMIA

A test was carried out using ddY male mice of 22–25 g in body weight, one group consisting of 6 mice.

The body temperature of mice was approximately 38° C. before the test. At 4 hours after intraperitoneal administration of reserpine in an amount of 5 mg/kg the body temperature of mice was reduced by approximately 8° C. in average. The test compound was simultaneously orally administered with 5 mg/kg of reserpine, and the degree of antagonistic effect of the test compound on the hypothermal action of reserpine was measured. This test has hitherto been the commonest method for evaluating anti-depressant activity.

When the hypothermal activity of reserpine was completely inhibited, the antagonistic activity was evaluated as 100%. Percentage (%) of an antagonistic activity was calculated by varying the doses of each test compound. In addition, a dose exhibiting 50% antagonistic activity, i.e. $ED_{50}$, of each compound was calculated by Litchfield-Wilcoxon method described in J. Pharmacol. Exp. Ther., 96, 99 (1949).

The activities of 8 compounds of the present invention are shown in Table 2. As a control, the activity of the known anti-depressive agent, amitripytline, is also shown in Table 2. Further, Table 2 also shows the acute toxicities, $LD_{50}$, in male mice.

TABLE 2

| Compound (Example No.) | $ED_{50}$ (mg/kg, p.o.) | $LD_{50}$ (mg/kg, p.o.) |
|---|---|---|
| 1 | 2.0 | 1170 |
| 4 | 1.8 | 1330 |
| 5 | 4.0 | 275 |
| 7 | 2.4 | — |
| 14 | 0.27 | 1110 |
| 15 | 2.9 | 1750 |
| 16 | 0.5 | 1400 |
| 20 | 1.5 | 370 |
| Amitriptyline | 14.5 | 380 |

B. PASSIVE AVOIDANCE RESPONSE FAILURE BY ELECTRIC SHOCK AS MODEL OF AMNESIA

The method described by Susan J. Sara in Psychopharmacology, 68, 235-241 (1980) was used as an amnesia model.

The test apparatus used, called as "Two Compartment Avoidance Box", consisted of a large lit compartment and a small dark compartment having a grid floor to which an electric current can be applied, these two compartments being painted black innerly and connected to each other Male Wistar rats of 170-220 g in body weight enter into the small box soon after they are introduced into the large box. When a rat enters into the small box, the inlet is closed and an electric current of 3 mA for 5 seconds is applied to the grid floor, so that the period for which the same rat does not enter into the small box is markedly prolonged when the rat is again introduced into the large box after 3 hours or more. This response is called as "passive avoidance response".

However, if an electric shock of 60 mA, 200 Hz for 0.8 second is given to the rat by electrodes set on both ears of the rat immediately after the rat comes out of the small box upon the application of the electric current, the "passive avoidance response" is inhibited. Indeed, the period for entering into the small box from the large box, latency, is shortened. This phenomenon is caused by loss of memory of the electric current applied from the grid floor by the electric shock. The shortened time of latency is used as an index of the loss of memory.

A memory improvement effect of a test compound is expressed in the degree of prolongation of latency (% improvement) in a test carried out 3 hours or more after the oral administration of the test compound after application of an electric shock.

The activities of three compounds of the present invention are shown in Table 3. The present compounds have a comparable activities as compared with a known nootropic agent, pieracetam.

TABLE 3

| Compound (Example No.) | Dose (mg/kg, p.o.) | Improvement (%) |
|---|---|---|
| 1 | 25 | 6.8 |
|  | 100 | 22.7 |
| 14 | 25 | 30.9 |
|  | 100 | 51.5 |
| 16 | 25 | 12.8 |
|  | 100 | 46.6 |
| Piracetam | 250 | 22.0 |
|  | 500 | 14.1 |

As is seen from the aforementioned data, the compounds of the invention will be useful for improving various depressive conditions including a psychosomatic disease, manic-depressive insanity and the like, and for improving higher dysfunction of the brain such as amnesia by presenile or senile dementia, encephalopathic sequelae and the like.

What is claimed is:

1. A thieno[2,3-d]pyrimidine compound represented by the formula (I):

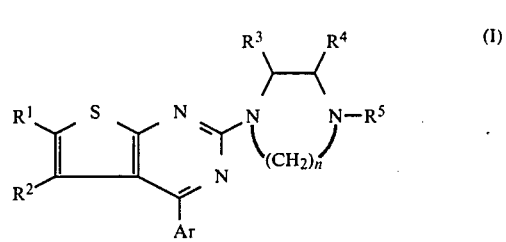

wherein $R^1$ and $R^2$ independently represent hydrogen, halogen or an alkyl group having 1-6 carbon atoms; or $R^1$ and $R^2$ together with the carbon atoms to which they are attached may form a cycloalkylene group having 5 to 6 carbon atoms; $R^3$ and $R^4$ independently represent hydrogen or an alkyl group having 1-6 carbon atoms; $R^5$ represents a member selected from the group consisting of:

(1) hydrogen or alkyl of 1-6 carbon atoms, and (2)

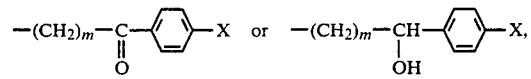

in which m is an integer of from 1 to 3 and X represents halogen;

Ar represents 2- or 3-thienyl, phenyl or phenyl substituted by a member selected from a group consisting of halogen, $C_1$-$C_6$ alkyl, $C_1$-$C_6$ alkoxy, hydroxyl, nitro, amino, cyano and alkyl-substituted amino; and n is 2; or a salt thereof.

2. The compound according to claim 1 wherein, in said substituted phenyl group, said halogen is fluorine, chlorine, bromine or iodine; said alkyl group is methyl, ethyl, propyl, butyl or hexyl; said alkoxy group is methoxy, ethoxy, propoxy or butoxy and said alkyl-substituted amino group is methylamino, ethylamino, dimethylamino or diethylamino.

3. The compound according to claim 1, wherein n is 2.

4. The compound according to claim 3, wherein $R^5$ is hydrogen.

5. The compound according to claim 4, wherein $R^4$ is hydrogen.

6. The compound according to claim 5, wherein $R^1$ is methyl or chloro and $R^2$ is hydrogen or methyl.

7. The compound according to claim 6, wherein $R^1$ is methyl and $R^2$ is hydrogen.

8. The compound according to claim 6, wherein Ar is unsubstituted phenyl or 2-fluorophenyl, 2-bromophenyl, 2-methylphenyl or 2-cyanophenyl group.

9. 6-Methyl-4-phenyl-2-piperazinyl-thieno[2,3-d]pyrimidine.

10. 5,6-Dimethyl-4-phenyl-2-piperazinyl-thieno[2,3-d]pyrimidine.

11. 5-Methyl-4-phenyl-2-piperazinyl-thieno[2,3-d]pyrimidine.

12. 6-Chloro-4-phenyl-2-piperazinyl-thieno[2,3-d]pyrimidine.

13. 4-(2-Fluorophenyl)-6-methyl-2-piperazinyl-thieno[2,3-d]pyrimidine.

14. 4-(2-Bromophenyl)-6-methyl-2-piperazinyl-thieno[2,3-d]pyrimidine.

15. 6-Methyl-4-(2-methylphenyl)-2-piperazinyl-thieno[2,3-d]pyrimidine.

16. 4-(2-Cyanophenyl)-6-methyl-2-piperazinyl-thieno[2,3-d]pyrimidine.

17. A pharmaceutical preparation for improving the depressive conditions and/or dysfunctions of the brain in a unit dosage form, which comprises an effective dosage of the thieno[2,3-d]pyrimidine compound according to claim 1 as an active ingredient.

18. A pharmaceutical composition for improving the depressive conditions and/or dysfunction of the brain, comprising:

an effective dosage of the thieno[2,3-d]pyrimidine compound according to claim 1 in association with a pharmaceutically acceptable carrier.

* * * * *